(12) United States Patent
March et al.

(10) Patent No.: US 7,456,416 B2
(45) Date of Patent: Nov. 25, 2008

(54) PLUG-IN RADIATION SOURCE MODULE FOR A WEATHERING APPARATUS

(75) Inventors: Peter March, Frankfurt (DE); Bernhard Borner, Freigericht (DE)

(73) Assignee: ATLAS Material Testing Technology GmbH (DE)

( * ) Notice: Subject to any disclaimer, the term of this patent is extended or adjusted under 35 U.S.C. 154(b) by 415 days.

(21) Appl. No.: 11/265,213

(22) Filed: Nov. 3, 2005

(65) Prior Publication Data

US 2006/0139931 A1 Jun. 29, 2006

(30) Foreign Application Priority Data

Nov. 17, 2004 (DE) .................. 20 2004 017 833 U

(51) Int. Cl.
*G01N 17/00* (2006.01)
*G01N 21/00* (2006.01)
*G21K 3/00* (2006.01)

(52) U.S. Cl. ............... 250/504 R; 250/492.1; 250/493.1; 250/365; 362/293; 362/294

(58) Field of Classification Search ............. 250/504 R, 250/492.1, 493.1, 365, 372; 362/293, 294
See application file for complete search history.

(56) References Cited

U.S. PATENT DOCUMENTS

| | | | | |
|---|---|---|---|---|
| 4,012,954 A | * | 3/1977 | Klippert | 73/150 R |
| 4,747,645 A | * | 5/1988 | Rudzki | 356/51 |
| 4,880,988 A | * | 11/1989 | Witt | 250/504 R |

FOREIGN PATENT DOCUMENTS

| | | |
|---|---|---|
| DE | G9100816 U1 | 5/1991 |
| DE | 10000770 A1 | 7/2001 |
| DE | 10155245 A1 | 5/2003 |

* cited by examiner

*Primary Examiner*—Nikita Wells
(74) *Attorney, Agent, or Firm*—Vedder Price P.C.

(57) ABSTRACT

A plug-in radiation source module (10) for mounting and locating a radiation source (3) for a weathering apparatus (20), the plug-in module (10) being configured to be insertable from without into a cavity (21) provided therefor in a weathering apparatus (20).

15 Claims, 5 Drawing Sheets

PLUG-IN RADIATION SOURCE MODULE FOR A WEATHERING APPARATUS

The present invention relates to a plug-in radiation source module for a weathering apparatus and to a correspondingly configured weathering apparatus. In such a weathering apparatus assessment of aging response due to weathering of a test specimen, particularly of a sheet test specimen, is performed by exposing it to artificial weathering. Such devices usually feature for this purpose a weathering chamber in which means for mounting the test specimens to be weathered and a source of radiation for irradiating the test specimens, particularly with ultraviolet radiation, are arranged.

A weathering apparatus is mainly intended to assess the life of materials which in application are continually exposed to the climate and thus deteriorate under climatic effects such as light and heat of the sun, moisture and the like. To obtain a good simulation of the climatic conditions it is of advantage when the spectral energy distribution of the light generated in the device corresponds as best possible to that of natural solar radiation, this being the reason why xenon radiators are often employed as the source of radiation in such devices. In addition an accelerated aging test of the materials is achieved substantially by irradiating the test specimens greatly intensified as compared to natural conditions to thus obtain an indication as to the long-term aging response of a material test specimens in relatively short time.

The majority of the material test specimens assayed in such a weathering apparatus are made of polymer materials in which the deterioration due to weathering is produced substantially by the UV component of solar radiation. The photochemical primary processes, i.e. photon absorption and the generation of excited conditions or free radicals involved in this are irrespective of the temperature whereas the subsequent steps in the reaction with the polymers or additives may be a function of the temperature, resulting in the observed aging of the materials likewise being a function of the temperature.

In weathering apparatuses known hitherto one or more ultra-violet radiation sources such as xenon radiation sources are usually employed, known to permit achieving a good simulation of the solar spectrum. However, halogen lamps as well as metal halogen lamps, fluorescent lamps or also UV LEDs can be employed just as well.

In any weathering apparatus the one or other of the radiation sources needs to be replaced from time to time. In conventional weathering apparatuses this is relatively complicated and a nuisance, because the radiation source needs to be installed within the weathering chamber at the intended location and contacted electrically. This is particularly relatively troublesome when the radiation source is a xenon radiator constituting an elongated glass envelope filled with xenon gas. To install or replace the radiation source the weathering chamber needs to be opened and the radiation source for replacement has to be disassembled under relatively cramped conditions to then be replaced by the new radiation source which needs to be electrically contacted, all of which requires at least some practice. The same hassle is experienced when changing the radiation filters which need to be located in suitable supporting devices before the radiation source. These too require manual insertion directly into the weathering chamber.

It is accordingly an object of the present invention to provide a device with which the radiation sources of a weathering apparatus can now be installed and replaced with no hassle.

This object is achieved by the features as shown in claim 1. Advantageous further embodiments and aspects form the subject matter of the sub-claims.

The invention provides a plug-in radiation source module for mounting and locating a radiation source for a weathering apparatus. The plug-in module is configured such that it can be simply inserted from without into a cavity provided therefor in a weathering apparatus.

The plug-in module is inserted into the opening provided therefor in the weathering apparatus and pushed into its plugged-in location in which the radiation source mounted in the plug-in module is oriented as desired relative to the test specimens to be irradaited so that the weathering apparatus can then be turned on directly thereafter.

Now, because the plug-in module can be handled independently of the weathering apparatus the procedure of inserting and replacing radiation sources is substantially facilitated. For this purpose the plug-in module merely needs to be withdrawn from the weathering apparatus and then under every conceivable and selectable ambient or lighting condition a radiation source is inserted in the plug-in module and electrically contacted or a radiation source is removed from the plug-in module and replaced by another one.

The plug-in radiation source module in accordance with the invention comprises preferably a housing within which the radiation source can be secured and plugged in electrically for which purpose two electrical contact terminals are applied to one end of the housing. When the plug-in module is fully inserted, these electrical contact terminals electrically contact the contact terminals provided within the weathering apparatus and connected to an electrical power supply. Thus, simply inserting the plug-in module produces the electrical contact for powering the radiation source contacted in the plug-in module.

In this arrangement the electrical contact terminals applied to the housing of the plug-in module are preferably provided as pins or plugs extending from the rear end of the housing in the direction in which the plug-in module is inserted. Provided within the weathering apparatus in the rear portion of the cavity are two socket contacts into which the pin contacts are inserted on insertion of the plug-in module. On insertion, the plug-in module is suitably guided so that the pin contacts of the plug-in module are inserted into the sokket contacts of the weathering apparatus. In the plugged-in location the plug-in module is fully inserted in the opening of the weathering apparatus and the pin contacts are correspondingly inserted in the socket contacts. As an alternative the terminals at both ends may also be formed by terminal pads.

Preferably provided at the front end of the plug-in module is a handle for inserting and removing the plug-in module into/from the weathering apparatus. In the removed condition the handle together with the front end of the housing can be removed for withdrawing and replacing the radiation source and, where necessary, the radiation filter lengthwise from the plug-in module.

A radiation reflector may be additionally integrated in the plug-in module. This radiation reflector may be made of sheet aluminum, for example, and designed to optimally reflect the radiation emitted by the radiation source in the direction of the test specimens arranged within the weathering apparatus.

The radiation source may constitute a xenon lamp, a (metal) halogen lamp, a fluorescent lamp or also one or more UV LEDs.

The housing of the plug-in module is configured box-shaped in particular, it thus comprising a bottom plate with side and end walls applied thereto in which the radiation reflector can be secured as a curved metallic shell with the housing box and the radiation source can be located within the plane of symmetry of the radiation reflector. The radiation source may be, for example, a xenon radiator in the form of an elongated glass envelope filled with xenon gas. In this case, the housing is likewise elongated, the radiation reflector being arranged therein and the xenon radiator located on the axis of symmetry of the radiation reflector.

Advantageously, it may further be provided for that a radiation filter can be inserted in a portion of the housing. For example, in two opposite sidewalls of the housing box, guide slots for mounting the radiation filter may be formed into which the radiation filter can be slotted from one end. These guide slots for the radiation filter may also be further configured to simultaneously serve guiding the plug-in module when inserted into the opening of the weathering apparatus. These, for example, may be formed by sheet metal outswept on both opposite sides of the housing, on the inner sides of which the radiation filter can be inserted and the outer contours of which form guide rails which are guided by the guide elements in the cavity of the weathering apparatus.

Since heat is developed by most radiation sources in a weathering apparatus, cooling air is usually introduced to discharge the heat from the radiation sources. For this purpose it may be provided for that the bottom plate of the housing box comprises at least one port for air inlet and a port for air outlet for passage of the cooling air. The air inlet port is provided at one end of the bottom plate whilst the air outlet port is provided at the other end of the bottom plate. Where an elongated radiation source is concerned, cooling air can thus be introduced at one end of the radiation source and directed along the radiation source to its other end where it is exhausted through an air outlet port. It may further be provided for that two air inlet ports are arranged in the bottom plate so that cooling air flows directly to and along the radiation source to the air outlet port and cooling air entering through the other air inlet port flows into the interspace between the radiation reflector and the housing wall and along the radiation reflector to the air outlet port.

The invention relates likewise to a weathering apparatus in which at least one plug-in radiation source module of the aforementioned kind is insertable. For this purpose the weathering apparatus preferably comprises a cavity dimenioned such that it can accommodate the plug-in module located in place and held substantially filling the space available. The cavity is open to the exterior so that the plug-in module can be inserted therein.

Preferably provided on the end wall of the cavity of the weathering apparatus opposite the insertion opening are the two electrical terminals of the weathering apparatus, further preferably configured as socket contacts into which the protruding pin contacts of the plug-in module can be inserted.

Furthermore, the weathering apparatus comprises preferably an air cooling system by means of which cooling air is introduced from one end into the cavity into the plug-in module inserted therein and exhausted at the other end of the cavity from the plug-in module inserted therein.

The plug-in module in accordance with the invention and the weathering apparatus will now be detailed by way of an example embodiment with reference to the FIGs. of the drawings in which.

Figure 2:
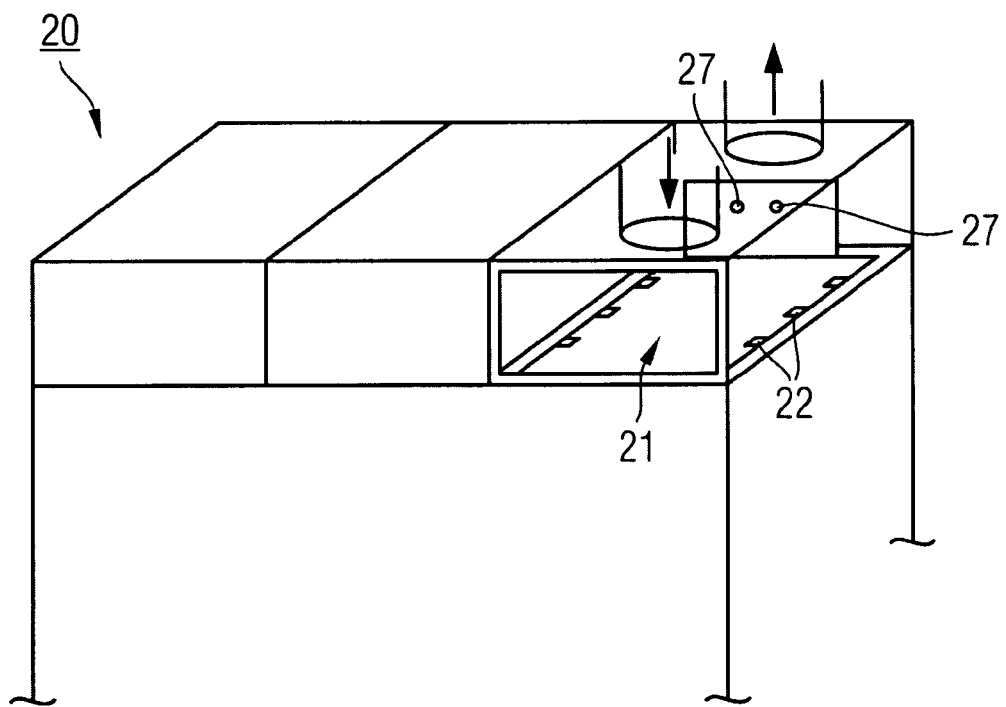
FIG. 2 is a illustration of an example embodiment for a weathering apparatus in accordance with the invention featuring a cavity for application of a plug-in module in accordance with the invention.

It is to be noted that the terms upper and lower as regards the plug-in module in accordance with the invention relate to the condition in which the plug-in module is inserted in the weathering apparatus as shown in FIG. 2.

In FIGS. 1a to 1e like components of the plug-in module in accordance with the invention are identified by like reference numerals.

Figure 1A:
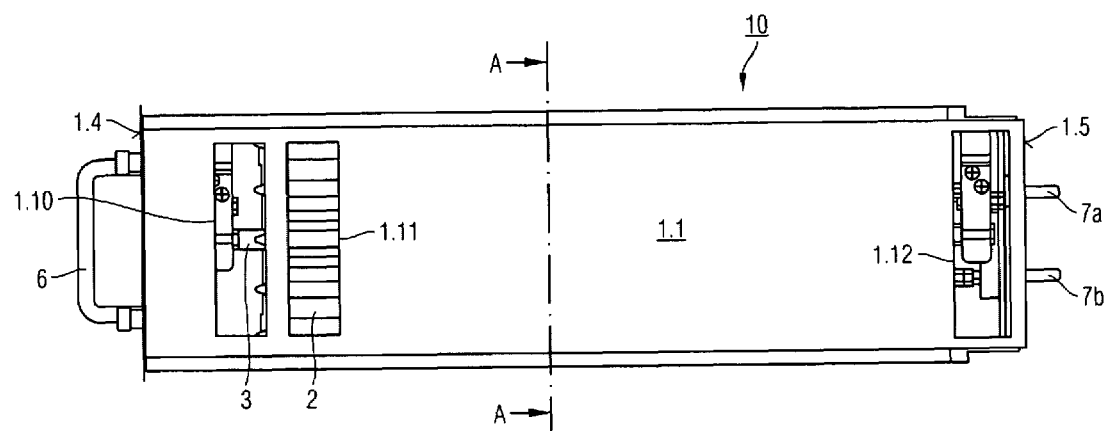
FIG. 1a is a plan view of a plug-in module in accordance with the invention.
Figure 1B:
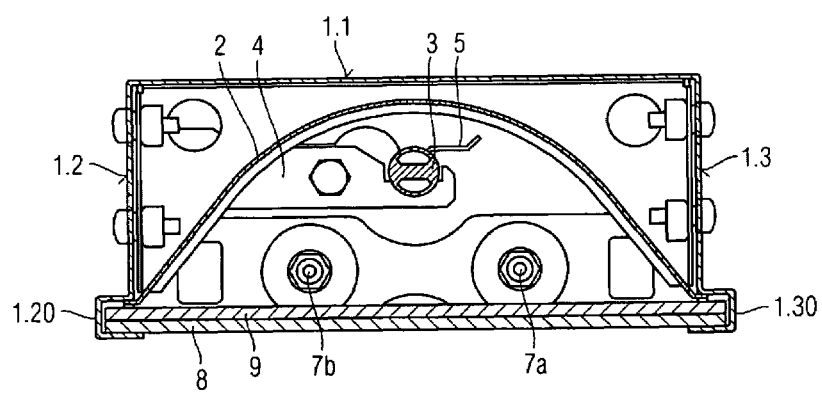
FIG. 1b is cross-section taken along the line A-A in FIG. 1a showing the plug-in module in accordance with the invention.

Referring now to FIG. 1b there is illustrated the box-shaped housing of the plug-in module 10 comprising a bottom plate 1.1 and side walls 1.2 and 1.3. The bottom plate 1.1 is located at the top so that in the plan view as shown in FIG. 1a it is fully illustrated. It comprises at its front end two air inlet ports 1.10 and 1.11 through which cooling air is introduced into the interior of the plug-in module 10 or housing of the plug-in module. Referring now to FIG. 2 there is indicated how by means of an air cooling system (not shown) of the weathering apparatus 20 the cooling air is introduced at the front end of the cavity 21 thereinto and thus into the two air inlet ports 1.10 and 1.11 of the plug-in module 10. Through the air inlet ports 1.10 the cooling air is supplied directly to the radiation source 3 of which only the front portion is evident in FIG. 1a through the air inlet port 1.10, whereas through the air inlet port 1.11 cooling air is directed to the radiation reflector 2 of which likewise in FIG. 1a again only a portion is evident through the air inlet port 1.11. Formed at the rear end of the bottom plate 1.1 is an air outlet port 1.12 through which the cooling air is blown or exhausted by the air cooling system of the weathering apparatus, as again indicated in FIG. 2. This results in the cooling air introduced through the air inlet ports 1.10 and 1.11 flowing both along the radiation source 3 and along the radiation reflector 2 up to the air outlet port 1.12 in thus ensuring effective cooling of the radiation source 3 and radiation reflector 2.

In the example aspect as shown, the radiation source 3 is formed by a xenon lamp provided in the form of an elongated glass envelope filled with xenon gas. The radiation source 3 extends within the plane of symmetry of the radiation reflector 2 which likewise extends in the longitudinal direction of the radiation source 3. Referring now to the cross-section as shown in FIG. 1b the radiation source 3 may be located for example ñ as shown ñ at the apex of the radiation reflector 2. It is supported at the front and rear end by plastics (PTFE) mounts secured to the side wall 1.2 of the housing of which only the rear mount is shown in cross-section in FIG. 1b. It is here that a spring tab 5 secured to the plastics mount 4 is evident to which the radiation source 3 is clamped in place by its narrow portion at its rear end.

Figure 1C:
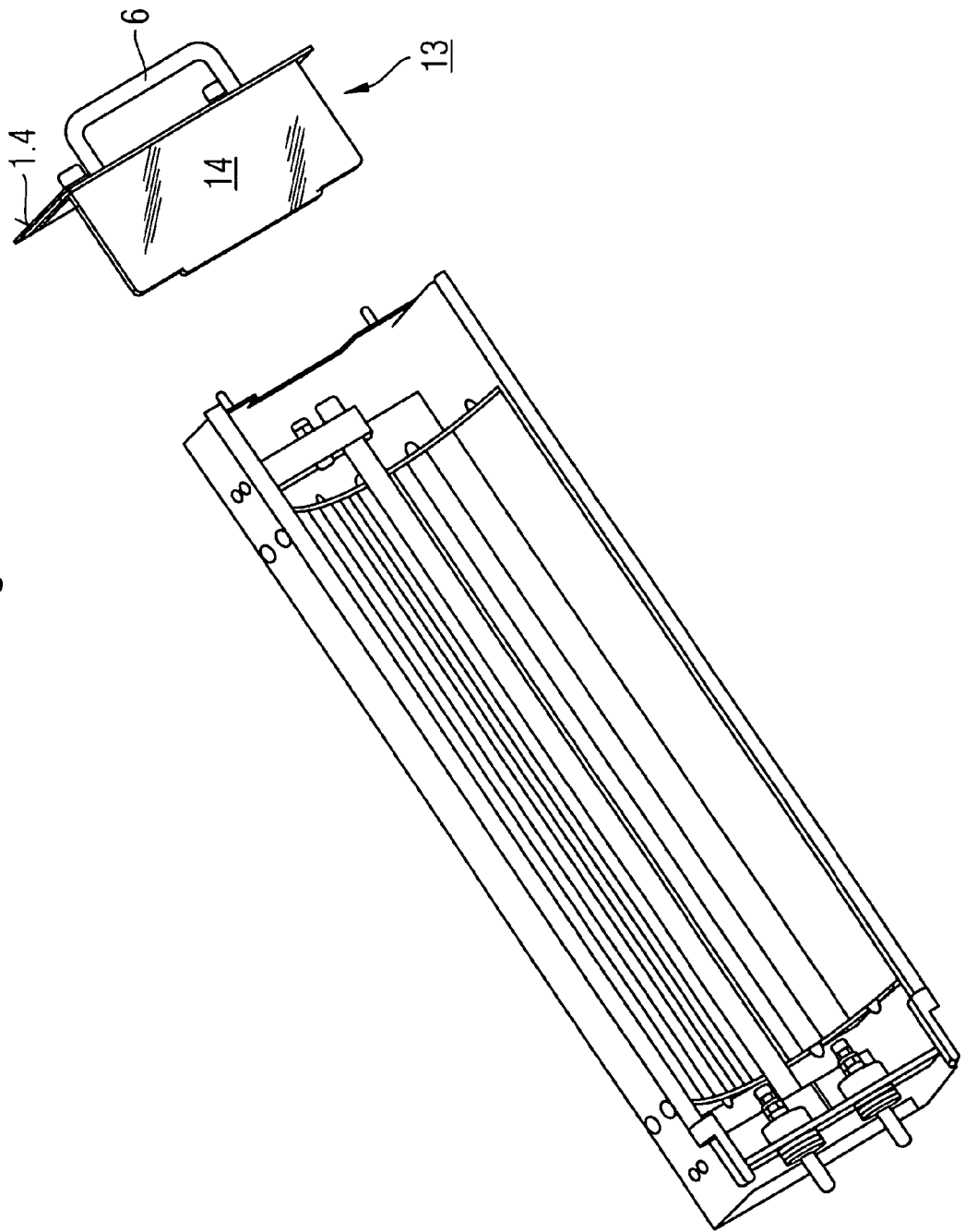
FIG. 1c is a view in perspective of the plug-in module in accordance with the invention taken at an angle from below for explaining how to remove the handle.
Figure 1D:
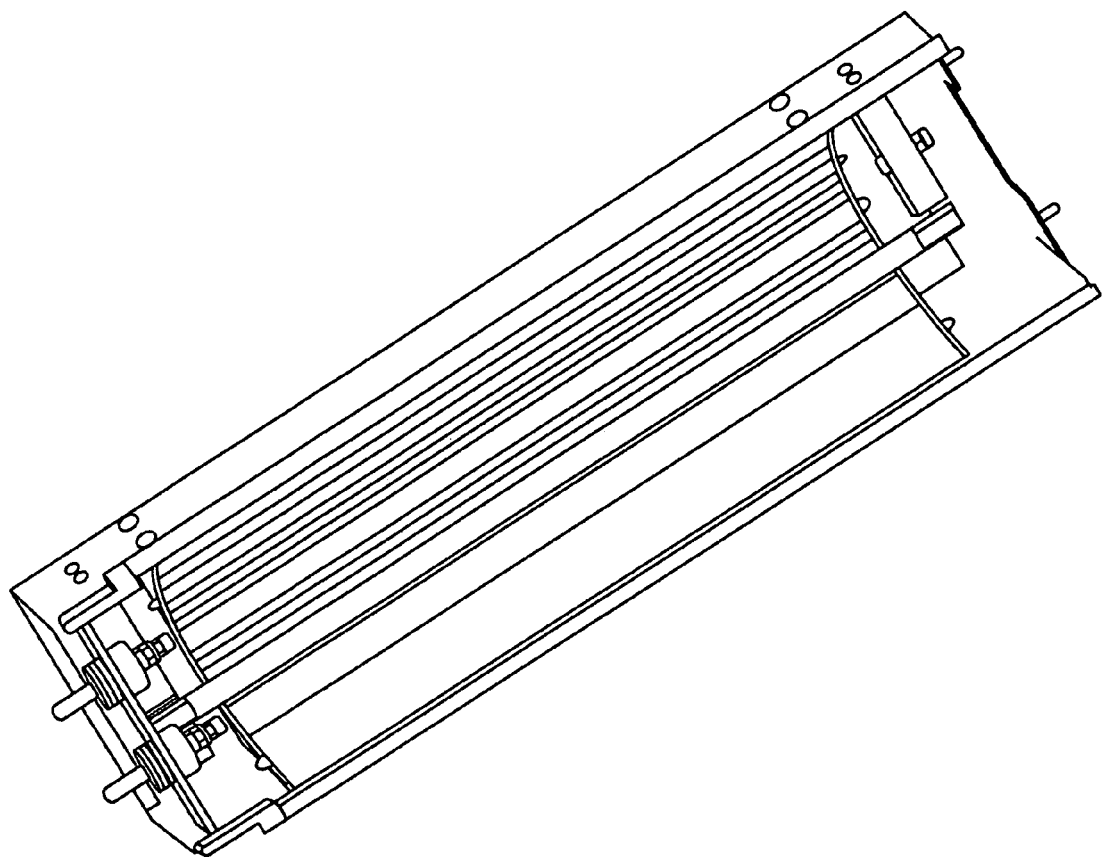
FIG. 1d is a view in perspective of the plug-in module in accordance with the invention taken at an angle from below showing the handle removed.

Secured to the front end wall 1.4 of the housing is a handle 6 with which the plug-in module can be inserted into the cavity 21 of the weathering apparatus 20 up to its plugged-in location and removed therefrom. Referring now to FIG. 1c there is illustrated how the handle 6 forms with the front end wall 1.4 and a lower wall portion 14 connected thereto at right angles a handle part 13 which is releasably screwed to the remaining part of the plug-in module. Referring now to FIG. 1d there is illustrated the handle part 13 in the released condition in which radiation filter and/or a xenon lamp can be installed or replaced as later explained.

Arranged at the end of the plug-in module opposite the handle 6 and front end wall 1. 4 on a housing end 1.5 the electrical pin contacts 7a and 7b extend from the housing end 1.5 in the same direction as the direction in which the plug-in module is inserted into the weathering apparatus. These pin contacts 7a and 7b are provided for insertion in the cavity 21 of the weathering apparatus 20, as shown in FIG. 2, into the socket contacts 27 provided at the rear end. The pin contacts 7a and 7b are connected within the plug-in module 10 to the terminal contacts at the front and rear end of the xenon radiator 3.

Figure 1E:
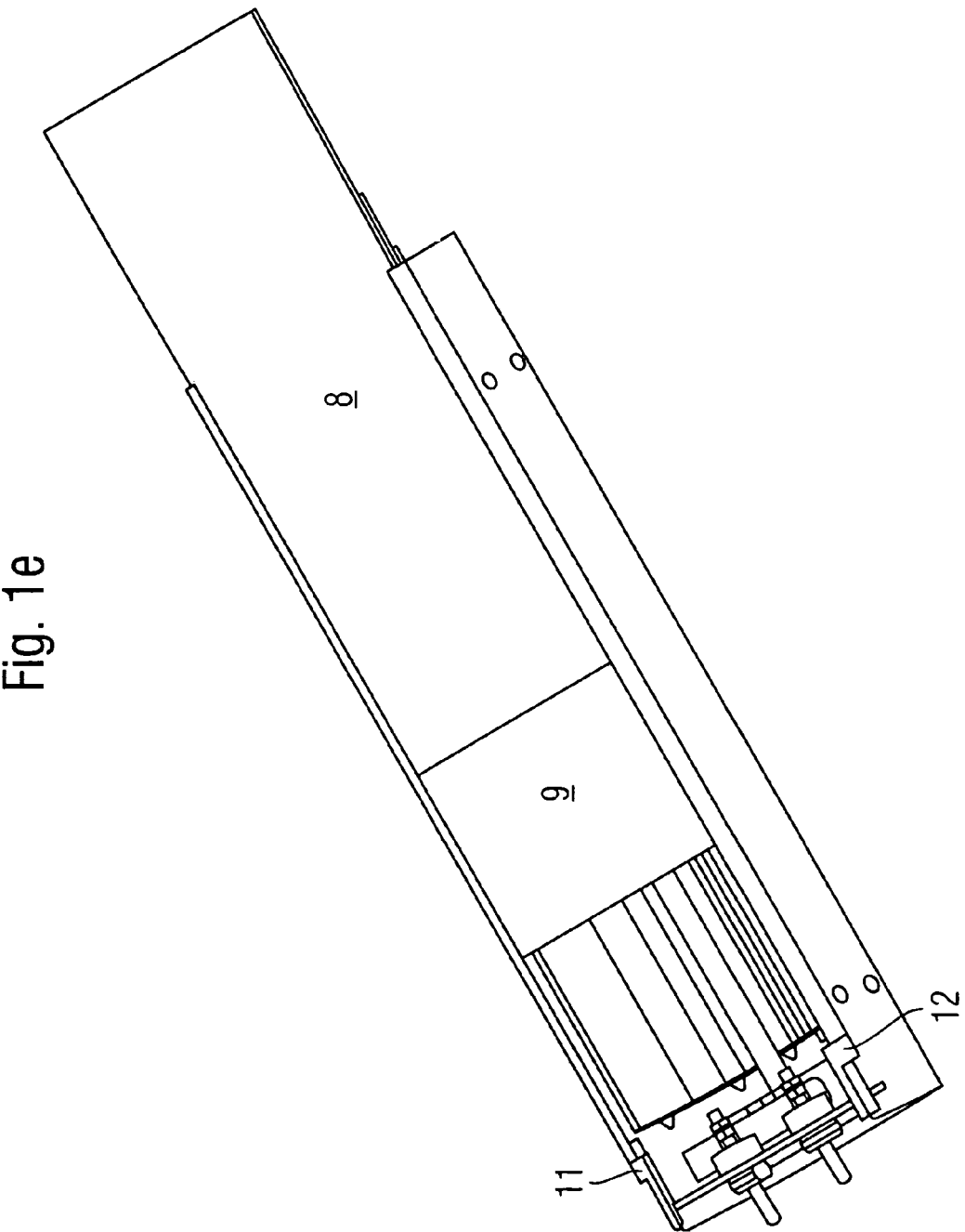
FIG. 1e is a view of the plug-in module in accordance with the invention taken at an angle from below for explaining how to insert two radiation filters.

Referring now to FIG. 1b there is illustrated formed at the side walls 1.2 and 1.3 at their lower ends guide slots 1.20 and 1.30 into which the radiation filters 8 and 9 can be inserted. These are usual radiation filters with which the UV component of the radiation emitted by the radiation source 3 is varied spectrally or filtered. The radiation filters may be made of modified window glass or also, however, of quartz glass or some other filter glass formulated as standard. Theoretically also an infrared filter glass can be inserted which, however, in practice is mostly located in the weathering apparatus at a specific suitable location. Referring now to FIG. 1e there is illustrated how two radiation filters 8 and 9 are partly inserted in the guide slots 1.20 and 1.30. The slots are defined at the rear end by plastics (PTFE) stoppers 11 and 12 up to which the radiation filters 8 and 9 are inserted. At the front end the handle part 13 is then refitted and screwed in place, the lower wall portion 14 being inserted into the guide slots 1.20 and 1.30 in defining the radiation filters 8 and 9 at the front end.

To replace either the xenon radiator 3 or the radiation filters 8 and 9 the plug-in module 10 is withdrawn from the weathering apparatus 20 and the handle part 13 unscrewed, after which the xenon radiator 3 can be released by disconnecting the electrical contacts and actuating the spring tab 5 for removal from the front end of the plug-in module 10 and replaced by a new xenon radiator 3. In the same way radiation filters 8 and 9 ñ where provided ñ can be withdrawn from the guide slots 1.20 and 1.30 and replaced new. In conclusion the handle part 13 is rescrewed in place and the plug-in module 10 can then be reinserted into the weathering apparatus 20.

The guide slots 1.20 and 1.30 are formed such that they simultaneously serve as rails for guiding insertion of the plug-in module 10 into the cavity 21 of the weathering apparatus 20. For this purpose suitable guide elements 22 may be arranged at the lower side edges of the cavity 21, formed for example by plastics (PTFE) mounts along which the guide slots 1.20 and 1.30 run.

Referring now to FIG. 2 there is illustrated how the weathering apparatus 20 comprises three correspondingly configured cavities into each of which a plug-in module 10 in accordance with the invention can be inserted so that the weathering apparatus 20 can be equipped with a maximum of three xenon radiators for irradiating the material test specimens. By means of these three xenon radiators the radiation is emitted downwards with the aid of the radiation reflectors surrounding each of them so that material test specimens positioned on a lower bottom plate of the weathering apparatus 20 are homogenously irradiated spatially with radiation.

The invention claimed is:

1. A plug-in radiation source module for mounting and locating a radiation source for a weathering apparatus, the plug-in module being configured to be insertable from without into a cavity provided therefor in a weathering apparatus.

2. The plug-in module as set forth in claim 1, comprising a housing within which the radiation source can be secured and electrically contacted, two terminal contacts being applied to one end of the housing.

3. The plug-in module as set forth in claim 2, the terminal contacts being formed by pin contacts extending from the rear end of the housing in a direction the same as the direction in which the plug-in module is inserted.

4. The plug-in module as set forth in claim 1, a handle being applied to the front end of the plug-in module for inserting and withdrawing the plug-in module into/from the weathering apparatus.

5. The plug-in module as set forth in claim 1 or 2, a radiation reflector being integrated in the plug-in module.

6. The plug-in module as set forth in claim 2, the housing being box-shaped.

7. The plug-in module as set forth in claim 1, the radiation reflector being a curved sheet of metal secured within the housing box and the radiation source being located within the plane of symmetry of the radiation reflector.

8. The plug-in module as set forth in claim 2, a portion of the housing being suitable for mounting a radiation filter.

9. The plug-in module as set forth in claim 2 or claim 8, at two opposite side walls of the housing box guide slots being formed for mounting the radiation filters.

10. The plug-in module as set forth in claim 9, the guide slots being configured so that they simultaneously serve to guide the plug-in module on insertion into the cavity of the weathering apparatus.

11. The plug-in module as set forth in claim 6, the housing box comprising a bottom plate comprising at least one air inlet port and an air outlet port for passage of cooling air.

12. A weathering apparatus into which at least one plug-in module radiation source as set forth in claim 1 is insertable.

13. The weathering apparatus as set forth in claim 12, comprising an opening or a cavity dimensioned to accommodate the plug-in module substantially space-fillingly.

14. The weathering apparatus as set forth in claim 12 or 13, comprising two terminal contacts to contact the terminal contacts of the plug-in module.

15. The weathering apparatus as set forth in claim 12 or 13, comprising an air cooling system configured whereby cooling air can be introduced in the region of the air inlet ports of the inserted plug-in module thereinto and whereby used cooling air can escape in the region of the air outlet port of the inserted plug-in module or exhausted by the cooling air system.

* * * * *